US008644336B2

(12) United States Patent
Takada et al.

(10) Patent No.: US 8,644,336 B2
(45) Date of Patent: Feb. 4, 2014

(54) DIAGNOSTIC IMAGING APPARATUS, MEDICAL SYSTEM AND PROTOCOL MANAGING METHOD

(75) Inventors: Yoichi Takada, Otawara (JP); Fumiaki Teshima, Nasushiobara (JP)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 1333 days.

(21) Appl. No.: 11/338,698

(22) Filed: Jan. 25, 2006

(65) Prior Publication Data

US 2006/0242095 A1    Oct. 26, 2006

(30) Foreign Application Priority Data

Jan. 26, 2005    (JP) ................. 2005-017702

(51) Int. Cl.
   *H04J 3/16*         (2006.01)
(52) U.S. Cl.
   USPC ........................................ 370/466
(58) Field of Classification Search
   USPC ........................................ 370/466
   See application file for complete search history.

(56) References Cited

U.S. PATENT DOCUMENTS

| 6,275,721 | B1* | 8/2001 | Darrow et al. ............. 600/410 |
| 2002/0077862 | A1* | 6/2002 | Auer et al. ...................... 705/3 |
| 2004/0044279 | A1* | 3/2004 | Lewin et al. ................. 600/407 |
| 2007/0192478 | A1* | 8/2007 | Louie et al. .................. 709/224 |

FOREIGN PATENT DOCUMENTS

| JP | 2004-195122 | 7/2004 |
| JP | 2004-283410 | 10/2004 |
| JP | 2004-362054 | 12/2004 |

* cited by examiner

*Primary Examiner* — Mark Rinehart
*Assistant Examiner* — Christopher R Crompton
(74) *Attorney, Agent, or Firm* — Oblon, Spivak, McClelland, Maier & Neustadt, L.L.P.

(57) ABSTRACT

A diagnostic imaging apparatus includes a protocol alteration history recording unit, a protocol alteration information detecting unit and a protocol alteration information displaying unit. The protocol alteration history recording unit records alteration histories according to protocols as protocol alteration history data. The protocol alteration information detecting unit detects an alteration about a designated protocol as protocol alteration information in accordance with the protocol alteration history data. The protocol alteration information displaying unit displays the protocol alteration information.

14 Claims, 12 Drawing Sheets

| DATE&TIME | USER ID | PROTOCOL ID | PAS | SEQUENCE | PARAMETER | DATA (OLD) | DATA (NEW) |
|---|---|---|---|---|---|---|---|
| 2004/10/30 11:56 | 1234 | 0001 | Routine Brain | FSE+15_nBW_crt | TS | 25 | 27 |
| 2004/11/5 18:09 | 2345 | 0002 | DISTAL FOOT | FSE+18_nBW_crt | GAP | 0.62 | 0.6 |
| 2004/11/20 8:45 | 5432 | 0003 | L-Spine | FSE+12_fc | THK | 3.5 | 3.8 |
| 2004/11/23 20:30 | 1234 | 0001 | Routine Brain | FSE+15_nBW_crt | FOV | 25×20 | 25×22 |
| 2004/11/30 15:35 | 2345 | 0003 | L-Spine | FSE+12_fc | TR | 634 | 635 |

Weekly Protocol Tracking Report

PAS Changed This Week

| PAS Name | Sequence | Parm | Old Value | New Value | Date / Time | User |
|---|---|---|---|---|---|---|
| SPEEDER Brain | FSE+18_nB W_crt | SPDRR | 1.6,1,1 | 2,1,1 | 2004/10/14 14:36 | Lori |
| Pituitary G QD H | FSE+20_nB W_crt | MTX | 128x256 | 192x256 | 2004/10/14 14:43 | Lori |
| Thoracic Spine Study | FE3D5_ssfp | TR | 12 | 10 | 2004/10/22 08:15 | Peter |

PAS Added This Week
  none

PAS Deleted This Week
  none

FIG. 13

Weekly Protocol Tracking Report

(History for the Exam changed PAS)

| PAS Name | # Used "as is" | # Used "ad-hoc" |
|---|---|---|
| SPEEDER Brain | 23 | 2 |
| Pituitary G QD H | 33 | 1 |
| Thoracic Spine Study | 14 | 0 |

| Date | Start Time | Study ID | Body Region | PAS Name | Exam Time | Scan # |
|---|---|---|---|---|---|---|
| 2004/10/14 | 10:04 | 3674.5581 | Head | SPEEDER Brain | 30 | 8 |
| 2004/10/16 | 15:32 | 3375.5581 | Head | SPEEDER Brain | 28 | 8 |
| 2004/10/22 | 13:33 | 3980.5581 | Head | Pituitary G QD H | 25 | 9 |

FIG. 14

DIAGNOSTIC IMAGING APPARATUS, MEDICAL SYSTEM AND PROTOCOL MANAGING METHOD

BACKGROUND OF THE INVENTION

1. Field of the Invention

The present invention relates to a diagnostic imaging apparatus, a medical system and a protocol managing method which can manage a history according to an alteration, a modification and so on of a scanning plan or a protocol.

2. Description of the Related Art

One type of diagnostic imaging apparatus is an MRI (magnetic resonance imaging) apparatus. The MRI apparatus is controlled by a scan plan or a protocol which is defined by a sequence for prescribing a imaging condition. The total number of sequence types in the MRI apparatus is approximately 3,000. Further, the total number of parameter items for setting a single sequence in the MRI apparatus is approximately 80.

The sequences are combined, thereby creating a PAS (Programmable Anatomical Scan) corresponding to an examination object. In general, the created PAS is classified as an examination object or an examination target, and is stored in a storage device in the MRI apparatus.

Further, a method or a system for setting parameters of a sequence that defines a protocol for the above-mentioned MRI apparatus has been suggested (see, for example, Japanese Patent Application (Laid-Open) No. 2003-225222).

With the above technique, parameters which can be set by an operator depending on an examination type, a imaging type, and a processing type are defined. Further, settable ranges of the parameters which can be set are limited. When selecting a predetermined imaging type or the like, only the parameters corresponding to the selected imaging type are provided in a controllable format.

However, the above-mentioned conventional MRI apparatus has such a problem that, when another operator inadvertently alters the parameter without involvement of the original operator, the original operator does not have means for knowing the alteration of the parameter. Moreover, the amount of information (the amount of information on 3,000 sequences× 80 parameters) on 80 parameter items in 3,000 sequence types is enormous. If it is known that the parameter is altered, it cannot be found easily which parameter in which sequence is altered.

Therefore, it is desired that altering information, such as an altering operator and altering date-and-time, inclusive of altering content of the sequence is acquired and is managed. Moreover, if the parameter of the sequence can be reset to the parameter before the alteration on the basis of the altering information, the improvement in convenience of the operator is expected.

In addition to that, the above-mentioned problem and demands for solution thereof are also common in a diagnostic imaging apparatus, such as an X-ray CT (computed tomography) apparatus, and a medical system, such as an HIS (hospital information system), as well as the MRI apparatus.

SUMMARY OF THE INVENTION

The present invention has been made in light of the conventional situations, and it is an object of the present invention to provide a diagnostic imaging apparatus, a medical system and a protocol managing method which can manage a history according to an alteration, a modification and so on of a scanning plan or a protocol.

The present invention provides a diagnostic imaging apparatus comprising: a protocol alteration history recording unit configured to record alteration histories according to protocols as protocol alteration history data; a protocol alteration information detecting unit configured to detect an alteration about a designated protocol as protocol alteration information in accordance with the protocol alteration history data; and a protocol alteration information displaying unit configured to display the protocol alteration information, in an aspect to achieve the object.

The present invention also provides a diagnostic imaging apparatus comprising: a protocol data storage unit configured to store protocols; a protocol parameter extracting unit configured to extract a selected protocol from the protocol data storage unit in accordance with selection information of the selected protocol; a protocol parameter storage unit configured to store the selected protocol extracted by the protocol parameter extracting unit; a protocol parameter recording unit configured to update a parameter of the selected protocol by altering the parameter and writing an altered protocol to the protocol data storage unit in case of receiving an input of alteration information to the parameter; and a protocol parameter alteration history recording unit configured to generate protocol alteration history data including an alteration history of the parameter by referring to the selected protocol before an alteration of the parameter and the altered protocol read from the protocol data storage unit, the selected protocol being stored in the protocol parameter storage unit, in an aspect to achieve the object.

The present invention also provides a medical system comprising: a protocol parameter storage unit configured to store a protocol extracted from a protocol data storage unit storing protocols in accordance with selection information of the protocol; and a protocol parameter alteration history recording unit configured to generate protocol alteration history data including an alteration history of a parameter of the protocol by referring to a protocol after an alteration of the parameter read from the protocol data storage unit and the protocol before the alteration of the parameter read from the protocol parameter storage unit, the protocol after the alteration of the parameter being altered in accordance with alteration information to the parameter and stored in the protocol data storage unit, in an aspect to achieve the object.

The present invention also provides a medical system comprising: a data acquisition unit configured to acquire protocol alteration history data indicating an alteration history about protocols for a diagnostic imaging apparatus in a hospital side from the diagnostic imaging apparatus, the data acquisition unit being provided in the hospital side; a data transfer unit configured to transfer the protocol alteration history data to a center side, the data transfer unit being provided in the hospital side; a data reception unit configured to receive the protocol alteration history data transferred from the data transfer unit, the data reception unit being provided in the center side; a protocol alteration history database configured to store the protocol alteration history data received by the data reception unit, the protocol alteration history database being provided in the center side; an alteration information detecting unit configured to detect an alteration about a designated protocol as protocol alteration information based on the protocol alteration history data stored in the protocol alteration history database, the alteration information detecting unit being provided in the center side; a report creation unit configured to create a report using the protocol alteration information and transmit the created report to the hospital side, the report creation unit being provided in the center side; and a hospital side client configured to receive the report transmitted from the report creation unit, the hospital side client being provided in the hospital side, in an aspect to achieve the object.

The present invention also provides a medical system comprising: a data reception unit configured to receive protocol alteration history data indicating an alteration history about protocols for a diagnostic imaging apparatus provided in a hospital side from the hospital side through a network, the data reception unit being provided in the center side; a protocol alteration history database configured to store the protocol alteration history data received by the data reception unit, the protocol alteration history database being provided in the center side; an alteration information detecting unit configured to detect an alteration about a designated protocol as protocol alteration information based on the protocol alteration history data stored in the protocol alteration history database, the alteration information detecting unit being provided in the center side; and a report creation unit configured to create a report using the protocol alteration information and transmit the created report to the hospital side, the report creation unit being provided in the center side, in an aspect to achieve the object.

The present invention also provides a protocol managing method comprising steps of: recording alteration histories according to protocols as protocol alteration history data; detecting an alteration about a designated protocol as protocol alteration information in accordance with the protocol alteration history data; and displaying the protocol alteration information, in an aspect to achieve the object.

The present invention also provides a protocol managing method comprising steps of: extracting a selected protocol from a protocol data storage unit storing protocols in accordance with selection information of the selected protocol; storing the selected protocol extracted; updating a parameter of the selected protocol extracted by altering the parameter and writing an altered protocol to the protocol data storage unit in case of receiving an input of alteration information to the parameter; and generating protocol alteration history data including an alteration history of the parameter by referring to the selected protocol stored before an alteration of the parameter and the altered protocol read from the protocol data storage unit, in an aspect to achieve the object.

The present invention also provides a protocol managing method comprising steps of: acquiring protocol alteration history data indicating an alteration history about protocols for a diagnostic imaging apparatus in a hospital side from the diagnostic imaging apparatus at the hospital side; transferring the protocol alteration history data from the hospital side to a center side; receiving the protocol alteration history data at the center side; storing the received protocol alteration history data at the center side; detecting an alteration about a designated protocol as protocol alteration information based on the stored protocol alteration history data at the center side; creating a report using the protocol alteration information at the center side and transmitting the created report to the hospital side; and receiving the report at the hospital side, in an aspect to achieve the object.

The present invention also provides a protocol managing method comprising steps of: receiving protocol alteration history data indicating an alteration history about protocols for a diagnostic imaging apparatus provided in a hospital side from the hospital side through a network at the center side; storing the received protocol alteration history data at the center side; detecting an alteration about a designated protocol as protocol alteration information based on the stored protocol alteration history data at the center side; and creating a report using the protocol alteration information at the center side and transmitting the created report to the hospital side, in an aspect to achieve the object.

The diagnostic imaging apparatus, a medical system and a protocol managing method as described above make it possible to manage a history according to an alteration, a modification and so on of a scanning plan or a protocol.

BRIEF DESCRIPTION OF THE DRAWINGS

In the accompanying drawings:

FIG. 13 is a diagram showing an example of a report generated by the protocol alteration history managing system shown in FIG. 11; and FIG. 14 is a diagram showing another example of a report generated by the protocol alteration history managing system shown in FIG. 11.

DESCRIPTION OF THE PREFERRED EMBODIMENTS

A diagnostic imaging apparatus, a medical system and a protocol managing method according to embodiments of the present invention will be described with reference to the accompanying drawings.

Figure 1:
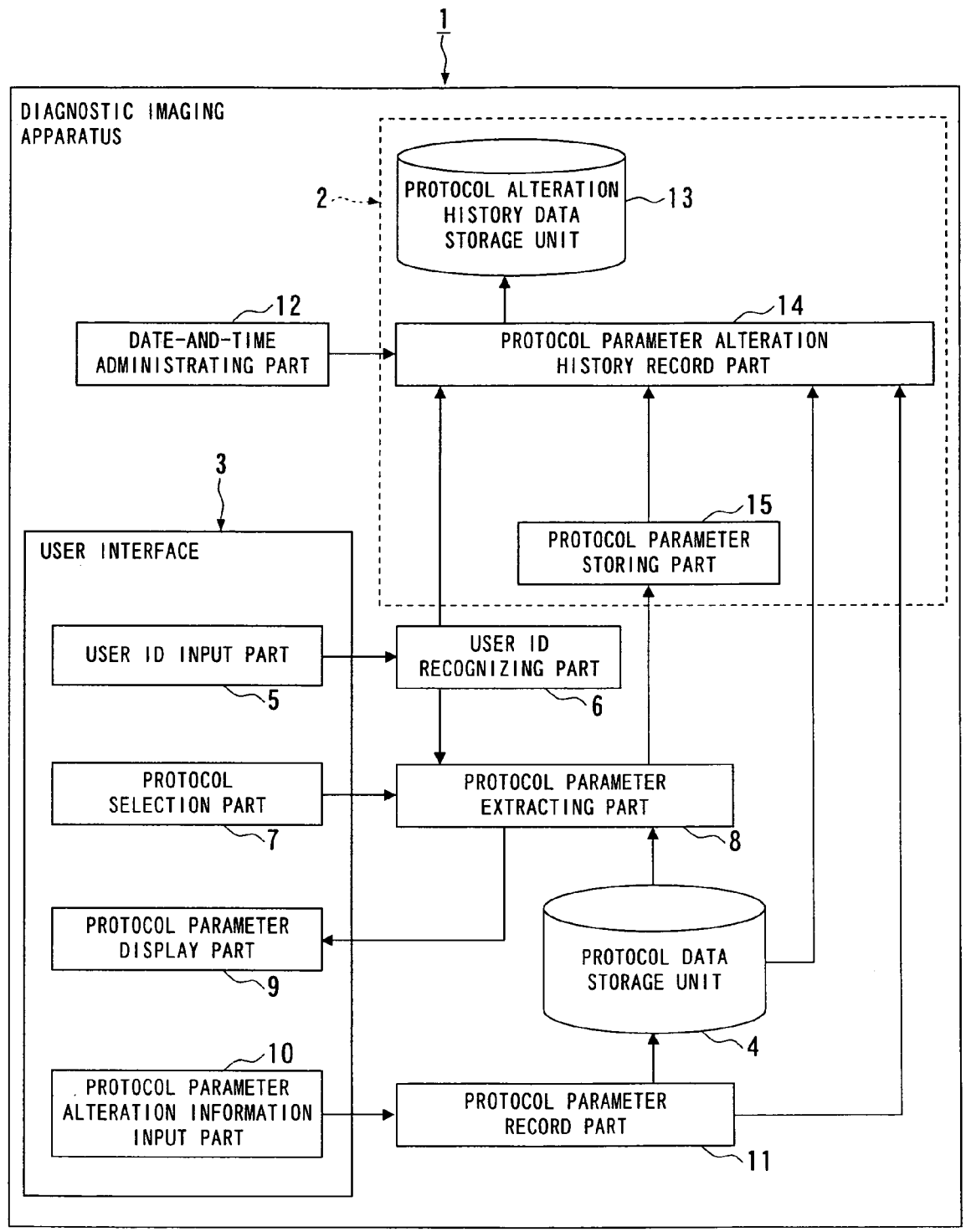
FIG. 1 is a functional block diagram showing a diagnostic imaging apparatus according to a first embodiment of the present invention.

FIG. 1 is a functional block diagram showing a diagnostic imaging apparatus according to a first embodiment of the present invention.

A diagnostic imaging apparatus 1 mounts a protocol alteration history managing system 2. The diagnostic imaging apparatus 1 also includes a user interface 3 built up with GUI (Graphical User Interface) technology.

The diagnostic imaging apparatuses 1 for mounting the protocol alteration history managing system 2 includes an ultrasonic diagnostic apparatus, an X-ray CT apparatus, an X-ray diagnostic apparatus, a nuclear medicine diagnostic apparatus and a MRI apparatus. Here, a MRI apparatus mounting the protocol alteration history managing system 2 will be described for example. The protocol alteration history managing system 2 can be mounted on not only the diagnostic imaging apparatuses 1 but also medical systems including a HIS, a RIS (radiology information system), a PACS (picture archiving and communication system) and an ASP (application service provider) system using networks to the outside of a hospital.

Note that, substantial difference between the case that an object mounting the protocol alteration history managing system 2 is a medical system and the case that an object mounting the protocol alteration history managing system 2 is a diagnostic imaging apparatus 1 is whether data are transmitted and received through networks while realization methods are mutually equivalent.

The diagnostic imaging apparatus 1 includes a protocol data storage unit 4, a user ID input part 5, a user ID recognizing part 6, a protocol selecting part 7, a protocol parameter extracting part 8, a protocol parameter display part 9, a protocol parameter alteration information input part 10, a protocol parameter record part 11 and a date-and-time administrating part 12. These elements are configured to work to alter parameters of protocols stored in the diagnostic imaging apparatus 1.

The protocol alteration history managing system 2 includes a protocol alteration history data storing unit 13, a protocol parameter alteration history record part 14 and a protocol parameter storing part 15. These elements give a function for storing alteration history of protocol parameters to the protocol alteration history managing system 2.

In addition, the user ID input part 5, the protocol parameter alteration information input part 10, the protocol parameter display part 9 and the protocol selecting part 7 form the user interface 3.

The protocol data storage unit 4 stores, in advance, protocols which can be used in the diagnostic imaging apparatus 1. Each protocol includes a protocol ID which is protocol identification information, a PAS name, a sequence name, a parameter name, and a data value of each parameter.

The user interface 3 includes the user ID input part 5. The user ID input part 5 receives inputs of a user ID and a password and sends the inputted user ID and password to the user ID recognizing part 6.

The user ID recognizing part 6 has a function for determining a user authority on the basis of the user ID and password inputted from the user ID input part 5, and a function for sending the determined user authority to the protocol parameter extracting part 8 and sending user identification information, such as the user ID, to the protocol parameter alteration history record part 14.

The user interface 3 further includes the protocol selection part 7. The protocol selection part 7 receives an input of a request for extracting the protocol, serving as a display target or an altering target, and sends the inputted request for extracting the protocol to the protocol parameter extracting part 8.

The protocol parameter extracting part 8 has a function for extracting the requested protocol from the protocol data storage unit 4 in response to the request for extracting the protocol which is inputted from the protocol selection part 7 and a function for sending the extracted protocol to the protocol parameter display part 9 and the protocol parameter storing part 15. When the protocol is extracted by the protocol parameter extracting part 8, the user authority received from the user ID recognizing part 6 is referred to by the protocol parameter extracting part 8 and it is checked to see if the user has an access authority to the requested protocol.

The user interface 3 further includes the protocol parameter display part 9 for displaying the parameters of the protocol received from the protocol parameter extracting part 8.

The protocol parameter storing part 15 has a function for holding the protocol received from the protocol parameter extracting part 8 and a function for sending the held protocol to the protocol parameter alteration history record part 14.

The user interface 3 further includes the protocol parameter alteration information input part 10. The protocol parameter alteration information input part 10 receives an input of altering information of the parameters of the protocol displayed on the protocol parameter display part 9 and sends the inputted altering information of the parameters of the protocol to the protocol parameter record part 11.

The protocol parameter record part 11 has a function for creating the protocol defined by new parameters in accordance with the altering information of the parameters of the protocol received from the protocol parameter alteration information input part 10 and updating the protocol by writing the created protocol after the alteration to the protocol data storage unit 4, and a function for sending a notification indicating that the protocol after the alteration is written to the protocol data storage unit 4, that is, the storage ends, to the protocol parameter alteration history record part 14.

The date-and-time administrating part 12 has a function for administering the date and time and sending a notification indicating a predetermined timing, e.g., date and time of the reception of the request of date-and-time information from the protocol parameter alteration history record part 14 to the protocol parameter alteration history record part 14.

The protocol parameter alteration history record part 14 has a function for detecting the altered parameters of the protocol by reading the protocol after the update stored in the protocol data storage unit 4 and the original protocol before the update temporarily-stored in the protocol parameter storing part 15 and comparing both the protocols, and a function for generating protocol alteration history data on the basis of the detecting result.

The protocol alteration history data can include information necessary from the presence or absence of the alteration of the protocol, the name of the altered protocol, identification information of the altered protocol, the name of the sequence forming the altered protocol, the name of the altered parameters, the data values before/after the alteration of the altered parameters, information on the date and time for altering the parameters of the protocol, the name of the user who alters the parameters of the protocol, identification information of the user who alters the parameters of the protocol, and the altering reason of the parameters. That is, the protocol parameter alteration history record part 14 has a function for generating the protocol alteration history data by adding arbitrary information to the values of the parameters before/after the alteration.

Therefore, the protocol parameter alteration history record part 14 has a function for requesting the date-and-time information to the date-and-time administrating part 12 and acquiring the date and time of a predetermined timing. Further, the user ID of the user who alters the parameters can be acquired from the user ID recognizing part 6. Further, the altering reason of the parameters can be received from an input device (not shown) by the protocol parameter alteration history record part 14 and can be included in the protocol alteration history data.

Moreover, the protocol parameter alteration history record part 14 has a function for writing the generated protocol alteration history data to the protocol alteration history data storage unit 13.

Thus, the protocol alteration history data storage unit 13 stores the protocol alteration history data generated by the protocol parameter alteration history record part 14.

Next, the operation of the diagnostic imaging apparatus 1 will be described.

Figures 2, 3:
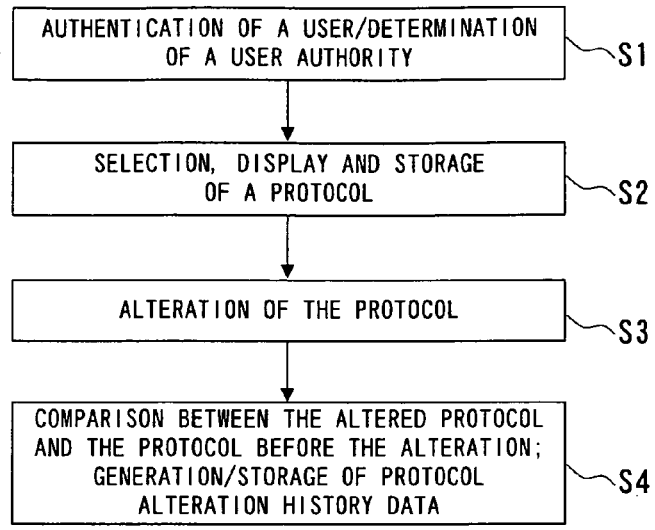
FIG. 2 is a flowchart showing a flow for storing a protocol alteration history by the diagnostic imaging apparatus shown in FIG. 1.
FIG. 3 is a diagram showing an example of protocol alteration history data stored in the protocol alteration history data storage unit of the diagnostic imaging apparatus shown in FIG. 1.

FIG. 2 is a flowchart showing a flow for storing a protocol alteration history by the diagnostic imaging apparatus 1 shown in FIG. 1. The symbols each including S with a number in FIG. 2 indicate steps of the flowchart respectively.

In step S1, the user ID and password of the user are inputted to the user ID input part 5. Then, the inputted user ID and password are sent to the user ID recognizing part 6. The user ID recognizing part 6 determines the user authority of the user on the basis of the inputted user ID and password. That is, the user ID recognizing part 6 determines an accessible range of the protocol and authorities, such as a browsing authority and a registering and correcting authority set to each user ID. Further, the user ID recognizing part 6 sends a notification indicating the determined user authority to the protocol parameter extracting part 8, and sends the inputted user ID to the protocol parameter alteration history record part 14.

When the access authority to the protocol is authenticated to the user, the user can display a protocol selecting screen and then can select a single or a plurality of arbitrary protocols.

Subsequently, in step S2, the protocol selecting screen is displayed, and the user refers to the displayed protocol selecting screen and simultaneously inputs the request for extracting the protocol, serving as the display target or altering target, to the protocol selection part 7. As the request for extracting the protocol, it is possible to use information, e.g., the protocol ID which is the identification information of the protocol, the PAS name, and the sequence name.

Then, the inputted request for extracting the protocol is sent to the protocol parameter extracting part 8. The protocol parameter extracting part 8 refers to the user authority received from the user ID recognizing part 6, and extracts the requested existing protocol from the protocol data storage unit 4 when the access authority to the requested protocol is authenticated to the user.

The extracted protocol is sent to the protocol parameter display part 9 and the protocol parameter storing part 15. As a result, the selected protocol is displayed on the protocol parameter display part 9 in the user interface 3. Further, the existing protocol extracted by the protocol parameter extracting part 8 is temporarily stored in the protocol parameter storing part 15.

Subsequently, in step S3, a parameter of the protocol displayed on the protocol parameter display part 9 is altered. That is, the user refers to the protocol displayed on the protocol parameter display part 9 and simultaneously inputs the altering information of the parameter of the protocol to the protocol parameter alteration information input part 10.

Therefore, the protocol parameter alteration information input part 10 sends the inputted altering information of the parameter of the protocol to the protocol parameter record part 11, and the protocol parameter record part 11 creates the protocol defined by a new parameter in accordance with the altering information of the parameter of the protocol. Then, the created protocol after the alteration is written to and is stored in the protocol data storage unit 4. As a consequence thereof, the existing protocol stored in the protocol data storage unit 4 is updated.

In addition, the protocol parameter record part 11 sends a notification indicating the completion of updating the existing protocol stored in the protocol data storage unit 4, that is, the storage completes, to the protocol parameter alteration history record part 14.

Subsequently, in step S4, the protocol parameter alteration history record part 14 reads the protocol after the alteration stored in the protocol data storage unit 4 and the protocol before the alteration temporarily-stored in the protocol parameter storing part 15 and compares the protocol before the alteration with the protocol after the alteration. The protocol parameter alteration history record part 14 detects the altered parameters of the protocol, and generates the protocol alteration history data which is obtained by adding the information, such as the user ID of the user who changes the parameter, the altering date, and the altering time, to the values of the detected parameters after/before the alteration.

In addition, the accompanying information, such as the user ID, the altering date, and the altering time, is sent to the protocol parameter alteration history record part 14 from the date-and-time administrating part 12 or the user ID recognizing part 6. Further, the protocol parameter alteration history record part 14 writes the generated protocol alteration history data, to the protocol alteration history data storage unit 13, to be stored in the protocol alteration history data storage unit 13.

FIG. 3 is a diagram showing an example of protocol alteration history data stored in the protocol alteration history data storage unit 13 of the diagnostic imaging apparatus 1 shown in FIG. 1.

Referring to FIG. 3, the protocol alteration history data contains, e.g., the altering date-and-time of the parameters, the user ID of the user who alters the parameter, the protocol ID of the protocol including the altered parameter, the PAS name, the sequence name, the parameter name, the data value (Data old) of the parameter before the alteration, and the data value (Data new) of the parameter after the alteration, and is recorded on time series and is further stored.

Therefore, with the above-mentioned diagnostic imaging apparatus 1, in the case of altering a parameter of the protocol, it is possible to record and manage, as the protocol alteration history data, the data value of the parameter before/after the alteration, as well as the identification information of the user who alters the parameter and the altering date-and-time. As a consequence thereof, it is possible to easily check the altering part and the altering content in the diagnostic imaging apparatus 1 using a large number of protocols and parameters by using the protocol alteration history data for reference, even if partly altering the parameters.

Figure 4:
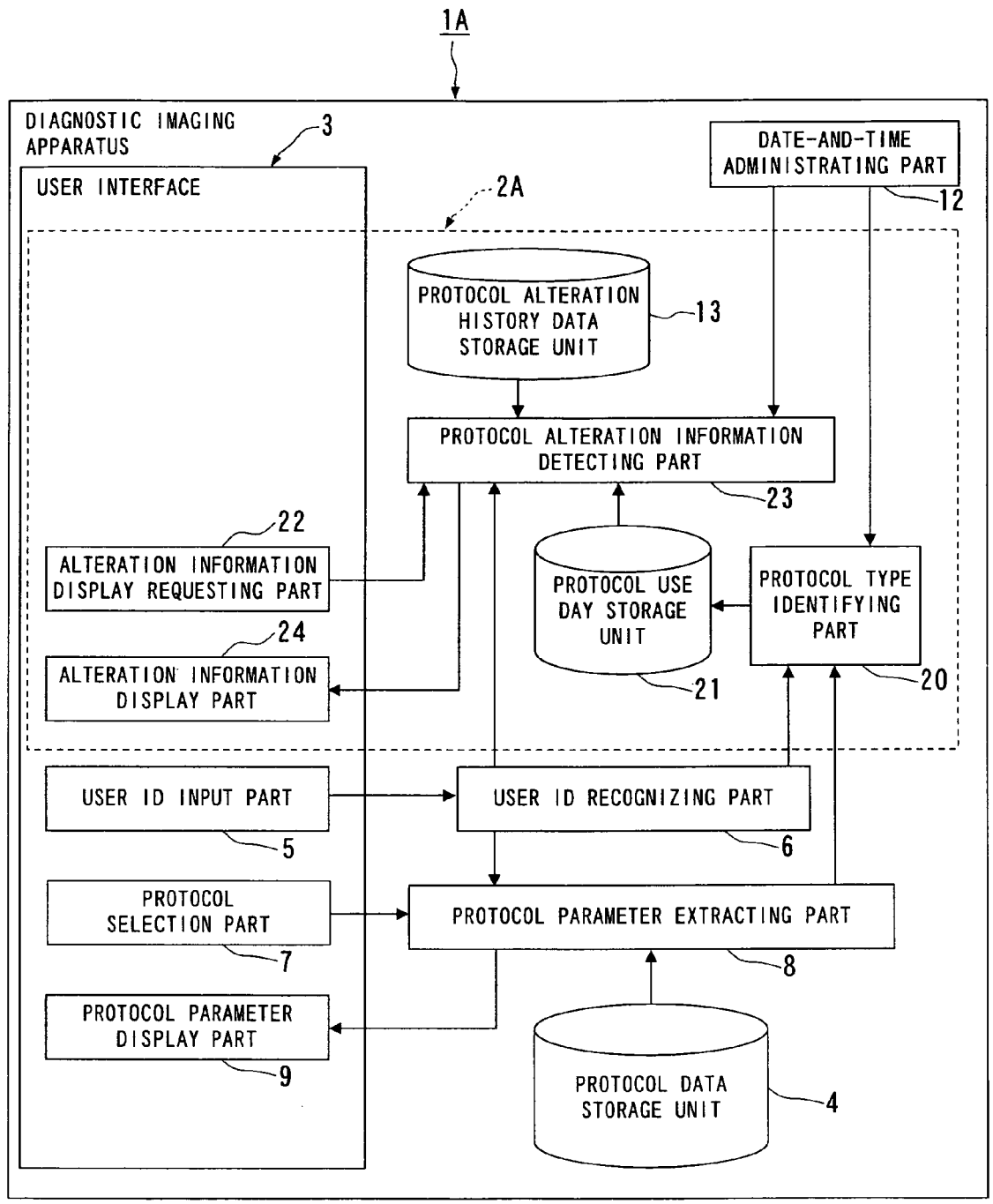
FIG. 4 is a functional block diagram showing a diagnostic imaging apparatus according to a second embodiment of the present invention.

FIG. 4 is a functional block diagram showing a diagnostic imaging apparatus according to a second embodiment of the present invention.

In the diagnostic imaging apparatus 1A shown in FIG. 4, terms that contents of alteration regarding the specific information specified by a user can be detected based on protocol alteration history data stored in the protocol alteration history data storage unit 13 and other necessary information to be displayed the detection result are different from those of the diagnostic imaging apparatus 1 shown in FIG. 1. Other constructions and operations of the diagnostic imaging apparatus 1A are not different from those of the diagnostic imaging apparatus 1 shown in FIG. 1 substantially. Therefore, same numbers are attached to the same components as those of the diagnostic imaging apparatus 1 to omit explanations thereof. Furthermore, showing elements according to processing up to storing protocol alteration history data is omitted.

A protocol alteration history managing system 2A of the diagnostic imaging apparatus 1A includes a protocol type identifying part 20, a protocol use day storage unit 21, a alteration information display requesting part 22, a protocol alteration information detecting part 23 and a alteration information display part 24 as well as the protocol alteration history data storing unit 13. These elements give a function for detecting contents of alteration regarding specific information specified by a user according to the protocol alteration history data to display the detection result to the protocol alteration history managing system 2A.

The protocol type identifying unit 20 has a function for associating the date and time for displaying the protocol by the user with the user ID and the identification information of the protocol based on the date-and-time information received from the date-and-time administrating part 12, the user ID received from the user ID recognizing part 6, and the protocol received from the protocol parameter extracting part 8 and further generating protocol use day information, and a function for writing the generated protocol use day information to the protocol use day storage unit 21.

Therefore, the protocol use day storage unit 21 stores the protocol use day information generated by the protocol type identifying unit 20.

The user interface 3 further includes the alteration information display requesting part 22 for receiving a request for displaying the protocol alteration information and sending the inputted request for displaying the protocol alteration information to the protocol alteration information detecting part 23.

The protocol alteration information to be displayed include alteration of protocol itself, alteration of the specific parameter in the past concerning on a certain protocol, alteration date-and-time of protocols or parameters, identification information of users who alter protocols or parameters and purposes and types of alteration. Purposes of alteration include alteration of quality of image, alteration of imaging period and alteration of imaging technique.

The protocol alteration information detecting part 23 has a function for detecting the corresponding protocol alteration information by retrieving the protocol alteration history data stored in the protocol alteration history data storage unit 13 the protocol use day information stored in the protocol use day storage unit 21 when the protocol alteration information detecting part 23 receives request for displaying protocol alteration information from the alteration information display requesting part 22 and a function for sending the detected protocol alteration information to the alteration information display part 24. Furthermore, if needed, the protocol alteration information detecting part 23 is configured to acquire the date-and-time information at an arbitrary time from the date-and-time administrating part 12.

More specifically, in case that the protocol alteration information which should be displayed is alteration of specific parameters, alteration date and time or identification information of users who alter the specific parameters for example, the protocol alteration information detecting part 23 retrieves whether or not the protocol alteration history data on the specific parameters which are requested to be displayed is stored in the protocol alteration history data storage unit 13. Furthermore, the protocol alteration information detecting part 23 acquires the user ID of the user who requests the display operation of the altered parameter from the user ID recognizing part 6 and further acquires the protocol use day information of the acquired user ID concerning on the corresponding protocol from the protocol use day storage unit 21. Then, the protocol alteration information detecting part 23 refers to the protocol alteration history data and the protocol use day information. In the case of satisfying a predetermined desired condition, the protocol alteration information detecting part 23 can detect protocol alteration information indicating alteration of the parameters.

On the other hand, in case that the protocol alteration information which should be displayed is alteration of parameters concerning specific alteration types (quality of image, imaging period or imaging techniques), the protocol alteration information detecting part 23 refers to the table formed by connecting types of alteration with the kinds of parameters previously in addition to the above-mentioned retrieval. If an altered parameter is concerned in the specific alteration type, the protocol alteration information detecting part 23 can detect protocol alteration information.

Furthermore, in case that the protocol alteration information which should be displayed is alteration of protocol itself, the protocol alteration information detecting part 23 retrieves the protocol use day information stored in the protocol use day storage unit 21 to detect alteration of the protocol serving as the protocol alteration information based on the protocol use day information of the corresponding user.

Note that, a retrieval range of the protocol alteration history data can be determined by a method of setting the protocol alteration history data of the specified period as the retrieval range or a method of setting the protocol alteration history data after the time at which the user logged in last time as the retrieval range as well as a method based on a user's use record of protocols, which is mentioned later. A retrieval range can be specified through the alteration information display requesting part 22. A use record of protocols can be acquired from the protocol use day information stored in the protocol use day storage unit 21. In addition, date-and-time information necessary for retrieval can be acquired from the date-and-time administrating part 12.

In this way, with the protocol alteration history managing system 2A, the protocol alteration information is dynamically detectable with designation of a user. The dynamic detection of protocol alteration information prevents deterioration of a user's convenience due to a function of displaying the protocol alteration information. For example, simply displaying the alteration history of all parameters as protocol alteration information may spoil user's convenience because of complicatedness of the displayed information. On the contrary, in the protocol alteration history managing system 2A, a user can designate the conditions for displaying the protocol alteration information arbitrarily so that only necessary alteration information is extracted and displayed. The user interface 3 includes the alteration information display part 24 for displaying the protocol alteration information received from the protocol alteration information detecting part 23.

Both the alteration information display part 24 and the protocol parameter display part 9 may display a list of the protocol having the altered parameters and the protocol having no altered parameters. In this case, when the alteration information display part 24 sets a display format, e.g., color or font, of one of the altered protocols and the altered parameters or both of them to be different from a display format of the non-altered protocols and parameters, based on the protocol alteration information received from the protocol alteration information detecting part 23, it is possible to identifiably display one of the altered protocols and the altered parameters or both of them.

Next, the operation of the diagnostic imaging apparatus 1A will be described. Here, the case where the protocol alteration information which should be displayed is alteration of a specific parameter will be described for example.

Figure 5:
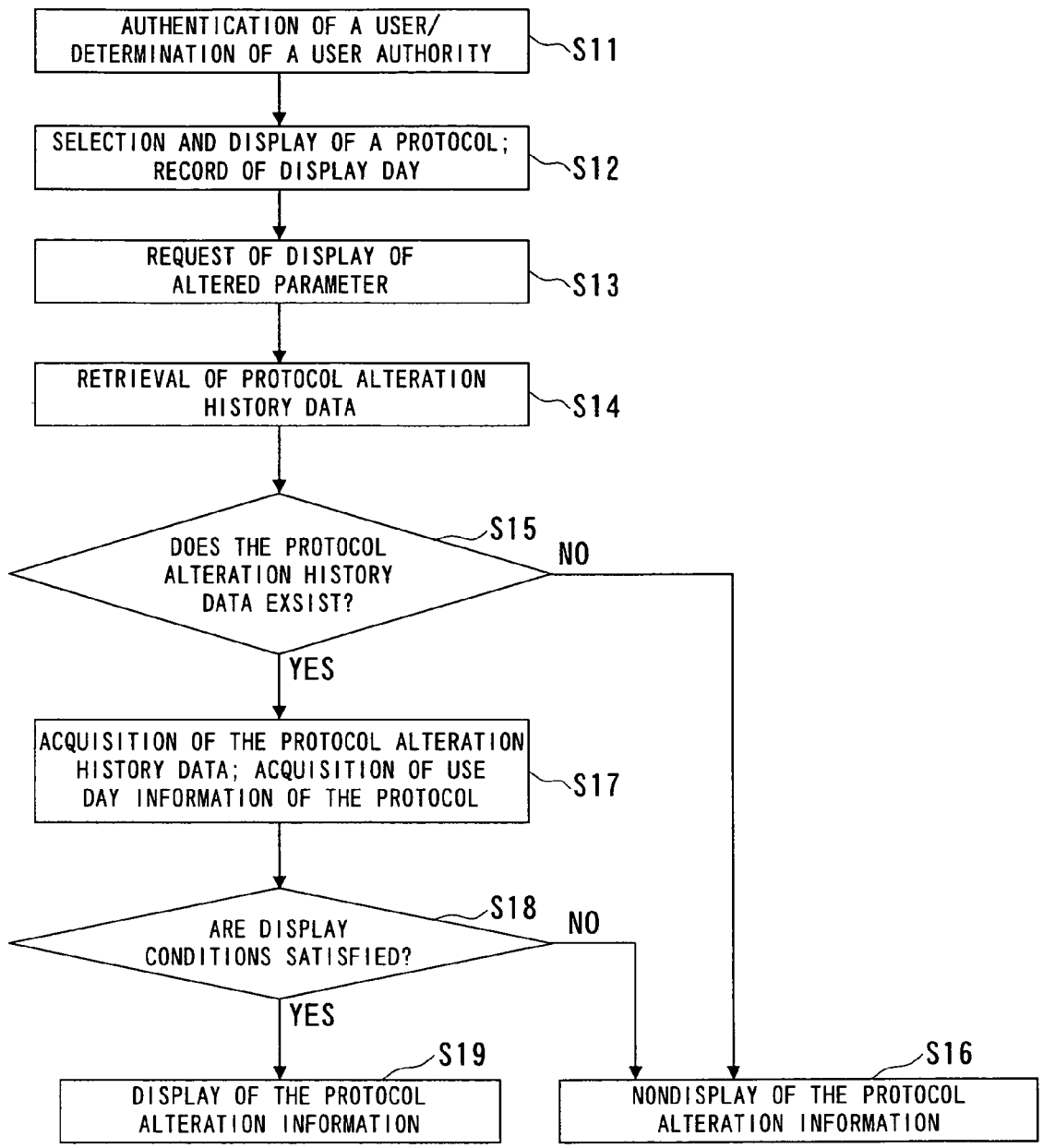
FIG. 5 is a flowchart showing a flow for displaying an altered specific parameter as protocol alteration information based on the protocol alteration history data stored in the protocol alteration history data storage unit by the diagnostic imaging apparatus shown in FIG. 4.

FIG. 5 is a flowchart showing a flow for displaying an altered specific parameter as protocol alteration information based on the protocol alteration history data stored in the protocol alteration history data storage unit 13 by the diagnostic imaging apparatus 1A shown in FIG. 4. The symbols each including S with a number in FIG. 4 indicate steps of the flowchart respectively.

In step S11, the user ID and password of the user are inputted to the user ID input part 5, and the user ID recognizing part 6 determines the user authority. The user authority is notified to the protocol parameter extracting part 8, and the user ID is sent to the protocol type identifying unit 20.

When the access authority to the protocol is authenticated to the user, the user can display the protocol selecting screen and can select a single or a plurality of arbitrary protocols.

Subsequently, in step S12, the protocol selecting screen is displayed and the user inputs a request for extracting the protocol, as a display target, to the protocol selection part 7 with referring to the displayed protocol selecting screen. Then, the inputted request for extracting the protocol is sent to the protocol parameter extracting part 8. The protocol parameter extracting part 8 refers to the user authority received from the user ID recognizing part 6 and finds whether the access authority to the requested protocol is authenticated to the user. If the access authority is authenticated to the user, the protocol parameter extracting part 8 extracts the existing protocol requested from the protocol data storage unit 4 and sends the extracted protocol to the protocol parameter display part 9 and the protocol type identifying unit 20. As a consequence thereof, the protocol parameter display part 9 in the user interface 3 displays the selected protocol.

The protocol type identifying unit 20 associates the date and time for displaying the protocol by the user with the user ID and the identification information of the protocol based on the date-and-time information received from the date-and-time administrating part 12, the user ID received from the user ID recognizing part 6, and the protocol received from the protocol parameter extracting part 8, to generate protocol use day information. Further, the protocol type identifying unit 20 writes the generated protocol use day information to the protocol use day storage unit 21 so as to be stored in the protocol use day storage unit 21.

As a result, the protocol use day information is written to the protocol use day storage unit 21 each time when the protocol is selected and is displayed. Then, the use date data for each protocol which was accessed and was displayed is stored and recorded every user ID on time series.

Figure 6:
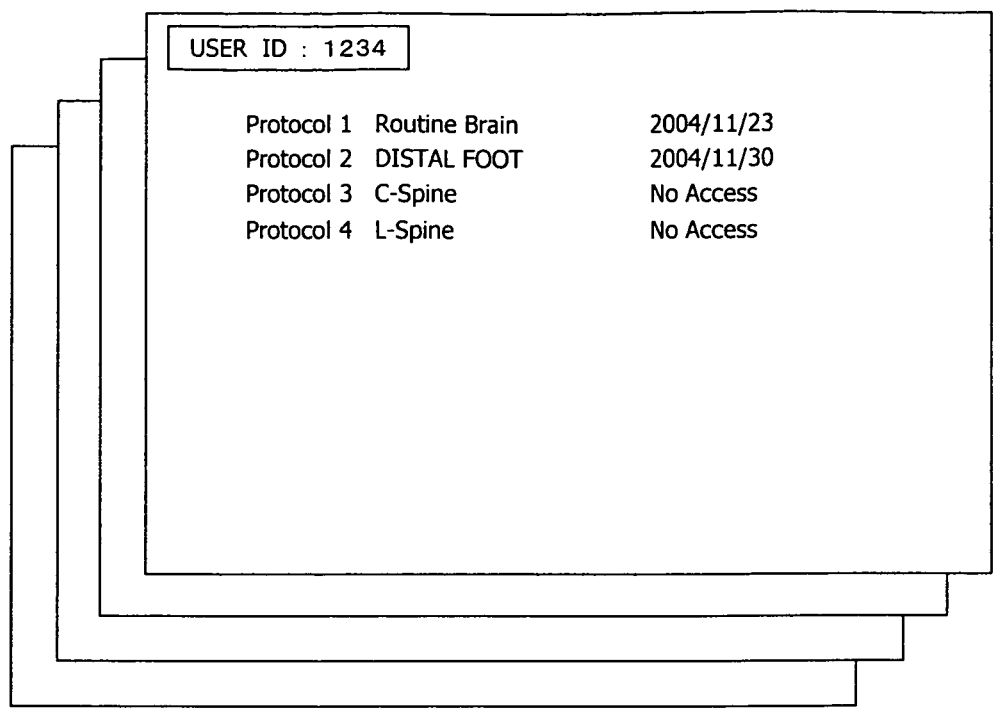
FIG. 6 is a diagram showing an example of protocol use day information recorded in the protocol use day storage unit of the diagnostic imaging apparatus shown in FIG. 4.

FIG. 6 is a diagram showing an example of protocol use day information recorded in the protocol use day storage unit 21 of the diagnostic imaging apparatus 1A shown in FIG. 4.

Referring to FIG. 6, the protocol use day information has a table for each user ID, which records the PAS name of the protocol accessed by the user and the access use date. Further, with respect to the non-accessed protocol, information indicating, e.g., "No Access" is recorded to the table.

Subsequently, in step S13, a request for displaying the altered parameters of the desired protocol is sent to the protocol alteration information detecting part 23 via the alteration information display requesting part 22. Then, in step S14, it is retrieved whether or not the protocol alteration history data about the altered parameters of which display operation is requested is stored in the protocol alteration history data storage unit 13.

Subsequently, in step S15, it is determined whether or not the protocol alteration history data storage unit 13 stores the protocol alteration history data about the altered parameters of which display operation is requested. If NO in step S15, the processing sequence advances to step S16 whereupon the protocol alteration information detecting part 23 sends Null information to the alteration information display part 24. As a result, the protocol alteration information is not displayed.

On the other hand, when it is determined in step S15 that the protocol alteration history data storage unit 13 stores the protocol alteration history data about the altered parameters of which display operation is requested, the processing sequence advances to step S17 whereupon the corresponding protocol alteration history data is read to the protocol alteration information detecting part 23 to be acquired. In addition to that, the protocol alteration information detecting part 23 acquires the user ID of the user who requests the display operation of the altered parameters from the user ID recognizing part 6, and acquires the protocol use day information of the corresponding protocol about the acquired user ID from the protocol use day storage unit 21.

Subsequently, in step S18, the protocol alteration information detecting part 23 determines, by referring to the protocol use day information and the protocol alteration history data, whether or not the predetermined display conditions of the protocol alteration information are satisfied. Then, if the determination of the display conditions of the protocol alteration information needs information at a predetermined timing, e.g., the current date-and-time information, the date-and-time administrating part 12 sends the current date-and-time information to the protocol alteration information detecting part 23.

When it is determined in step S18 that the display conditions of the protocol alteration information are not satisfied, in step S16, the protocol alteration information detecting part 23 sends the Null information to the alteration information display part 24. As a consequence thereof, the alteration information display part 24 does not display the protocol alteration information.

On the other hand, when it is determined in step S18 that the display conditions of the protocol alteration information are satisfied, in step S19, the protocol alteration information detecting part 23 sends the protocol alteration information to the alteration information display part 24. As a result, the alteration information display part 24 displays the protocol alteration information.

Note that, examples of the display conditions of the protocol alteration information include one that, the protocol alteration information is displayed when the protocol use day information about the corresponding protocol does not exist because it is assumed that the user has never displayed the corresponding protocol and, on the other hand, Null information is sent to the alteration information display part 24 and the protocol alteration information is not displayed when the protocol use day information exists but the use date of the protocol is after the altering date-and-time of the parameters determined based on the protocol alteration history data because it is assumed that the user has displayed the protocol after altering the parameters.

Examples of the display conditions using the protocol use day information include, in addition to the above-mentioned condition, e.g., one that, under a condition of the presence or absence of the use history of the user, the alteration information display part 24 displays the protocol alteration information detected based on only the protocol Further, other examples of the display conditions of the protocol alteration information include that, the protocol alteration history data is displayed as protocol alteration information when the protocol alteration history data is one within a predetermined period, e.g., one month after altering the specific parameter. In such a case, the altering date-and-time of the parameter which is determined based on the protocol alteration history data is compared with the date-and-time information at the present time (at the time for requesting the display operation) acquired from the date-and-time administrating part 12, thereby enabling the determination as whether or not the display conditions of the protocol alteration information are satisfied.

That is, if one month or more has elapsed, the Null information is sent from the protocol alteration information detecting part 23 without sending the protocol alteration history data about the altered parameters, which is not detection target of the protocol alteration information, to the alteration information display part 24. On the other hand, if one month or more does has never elapsed, the protocol alteration information detecting part 23 sends the protocol alteration information detected from the protocol alteration history data about the altered parameters to the alteration information display part 24.

Furthermore, other examples of display conditions of the protocol alteration information include that the alteration information display part 24 can display the protocol alteration information detected from the protocol alteration history data about the protocol having the parameters altered after previous log-in of the user, as described above. In this case, a user log-in history managing unit is provided to associate the identification information of the user with log-in date-and-time of the user and to store the associated information, as user log-in history. It can be determined, based on the user log-in history and the date-and-time information, whether or not the display conditions are satisfied.

Figure 7:
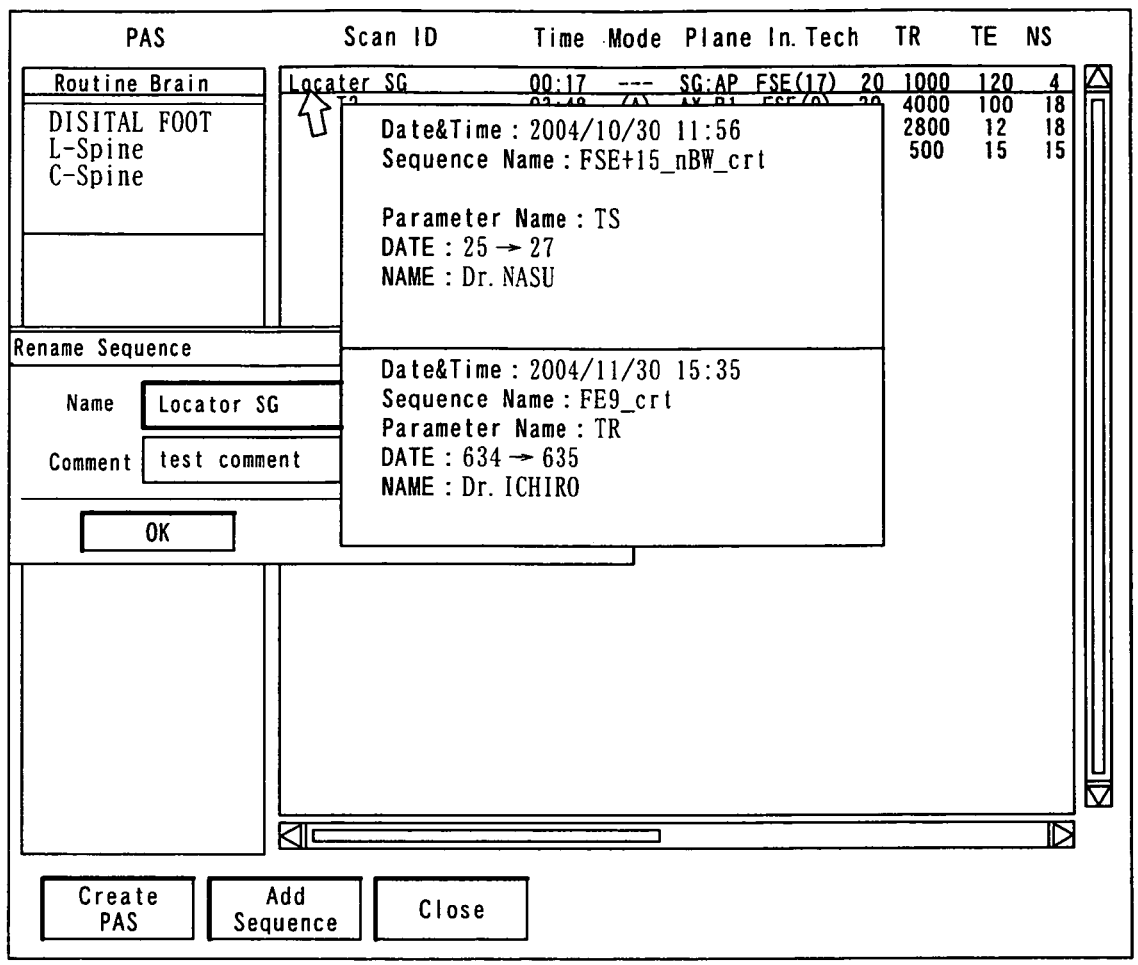
FIG. 7 is a diagram showing an example of protocol alteration information displayed on the alteration information display part of the diagnostic imaging apparatus shown in FIG. 4.

FIG. 7 is a diagram showing an example of protocol alteration information displayed on the alteration information display part 24 of the diagnostic imaging apparatus 1A shown in FIG. 4;

Referring to FIG. 7, a cursor is moved to select an arbitrary protocol, and the request for displaying the altered parameters about the selected protocol is sent to the protocol alteration information detecting part 23 via the alteration information display requesting part 22. Then, the protocol alteration information detecting part 23 retrieves whether or not the protocol alteration history data storage unit 13 stores the protocol alteration history data about a value of the parameter which is instructed by the cursor.

When the protocol alteration history data storage unit 13 does not store the protocol alteration history data about the value of the parameter which is instructed by the cursor, the protocol alteration information is not displayed. On the contrary, when the protocol alteration history data storage unit 13 stores the protocol alteration history data about the value of the parameter which is instructed by the cursor, with the satisfaction of the display conditions, the alteration information display part 24 displays the protocol alteration information including the altering date-and-time of the parameter, the sequence name, the parameter name, the data value after/before the alteration, and the identification information (e.g., user name) of the user who alters the parameter, based on the protocol alteration history data extracted by the protocol alteration information detecting part 23.

Therefore, with the diagnostic imaging apparatus 1A having the above-mentioned configuration, it is possible to extract the proper protocol alteration history data from the protocol alteration history data stored by the diagnostic imaging apparatus 1 shown in FIG. 1 in accordance with the desired conditions to be displayed as the protocol alteration information. Thus, the user can easily know the past altering fact and altering content of the protocols based on numerous combinations of (3,000 sequences×80 parameters). Further, the user can know not only the altering content but also information important to the altering management of the protocols, such as the identification information of the user who alters the parameter.

Moreover, with the diagnostic imaging apparatus 1A, it is possible to simply display the protocol alteration information in consideration of the past access situation of the user. For example, it can be prevented that the protocol alteration information which is displayed once is repeatedly displayed plural times and, further, it can be prevented that the protocol alteration information with a lapse of a predetermined period is displayed.

Figure 8:
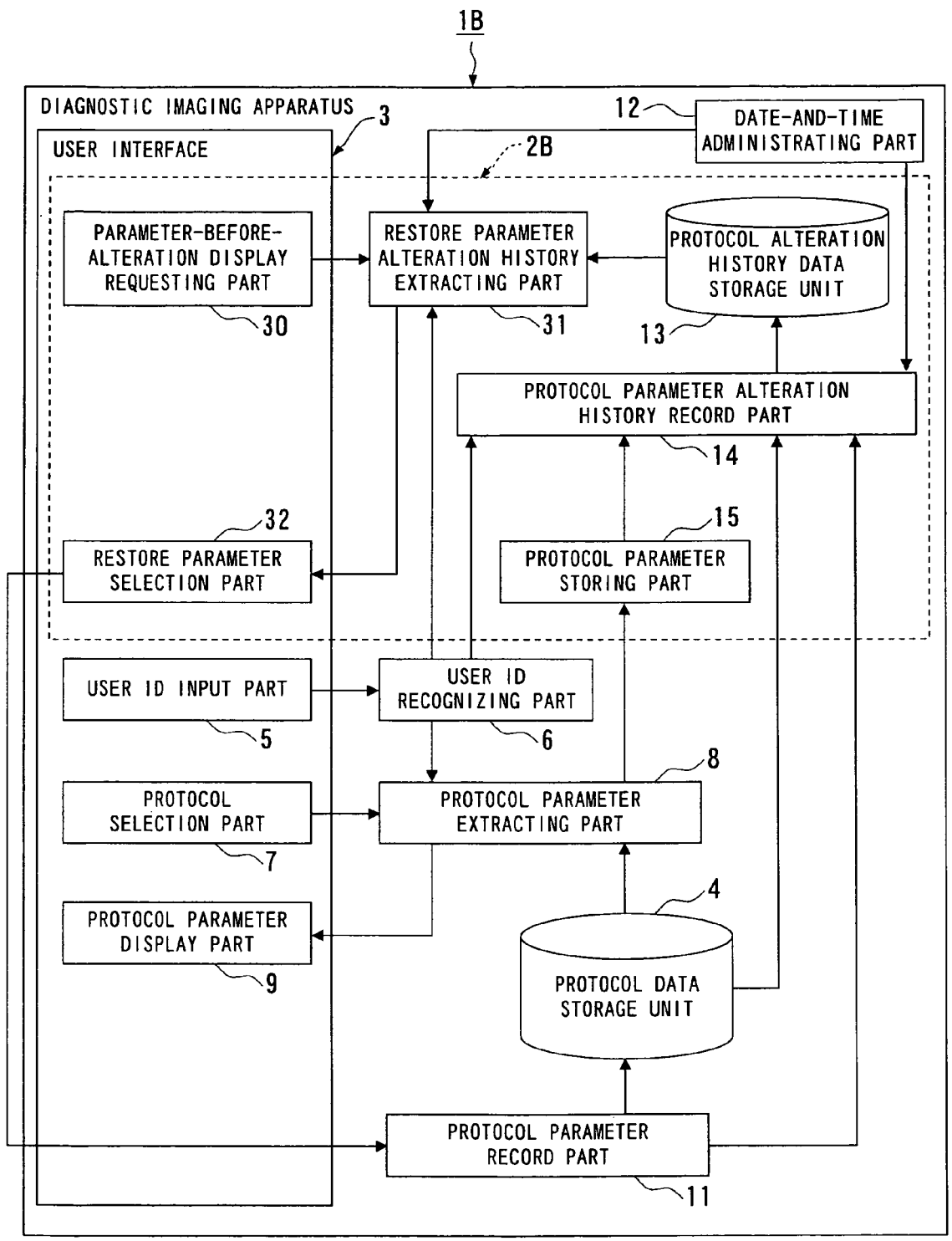
FIG. 8 is a functional block diagram showing a diagnostic imaging apparatus according to a third embodiment of the present invention.

FIG. 8 is a functional block diagram showing a diagnostic imaging apparatus according to a third embodiment of the present invention.

In the diagnostic imaging apparatus 1B shown in FIG. 8, terms that an altered parameter can be return to a parameter before alteration based on protocol alteration history data stored in the protocol alteration history data storage unit 13 are different from those of the diagnostic imaging apparatus 1 shown in FIG. 1. Other constructions and operations of the diagnostic imaging apparatus 1B are not different from those of the diagnostic imaging apparatus 1 shown in FIG. 1 substantially. Therefore, same numbers are attached to the same components as those of the diagnostic imaging apparatus 1 to omit explanations thereof. Furthermore, showing elements according to processing up to storing protocol alteration history data is omitted.

A protocol alteration history managing system 2B of the diagnostic imaging apparatus 1B includes a parameter-before-alteration display requesting part 30, a restore parameter alteration history extracting part 31 and a restore parameter selection part 32 as well as the protocol alteration history data storing unit 13, the protocol parameter alteration history record part 14 and the protocol parameter storing part 15. These elements give a function, to the protocol alteration history managing system 2B, for restoring the altered parameters to the parameters before alteration based on the protocol alteration history data stored in the protocol alteration history data storing unit 13.

The user interface 3 includes the parameter-before-alteration display requesting part 30 for inputting a request for displaying a list of parameters which can be restored to the parameters before the alterations among the parameters after the alterations of a single or a plurality of protocols and for sending the inputted request for displaying the list of the restorable parameters to the restore parameter alteration history extracting part 31.

The restore parameter alteration history extracting part 31 has a function for retrieving the protocol alteration history data storage unit 13 in accordance with the request for displaying the list of the restorable parameters inputted from the parameter-before-alteration display requesting part 30 and a predetermined condition and determining whether or not the parameters can be restored to acquire the protocol alteration history data about the corresponding restorable parameters and a function for sending the acquired protocol alteration history data or the list of the restorable parameters included in at least the protocol alteration history data to the restore parameter selection part 32.

Moreover, the restore parameter alteration history extracting part 31 acquires information on as whether or not the access authority to the corresponding protocols or parameters is authorized from the user ID recognizing part 6 and the date-and-time information at an arbitrary time from the acquired date-and-time administrating part 12, if needed, when determining whether or not the parameters can be restored.

The user interface 3 includes the restore parameter selection part 32 for displaying one of the protocol alteration history data inputted from the restore parameter alteration history extracting part 31 and the list of the restorable parameters or both of them, receiving an instruction for restoring a parameter, and sending the instruction to the protocol parameter record part 11. Further, the restore parameter selection part 32 allows the protocol parameter record part 11 to restore the parameter after the alteration, stored in the protocol data storage unit 4, to the parameter before the alteration.

Next, the operation of the diagnostic imaging apparatus 1B will be described.

Figure 9:
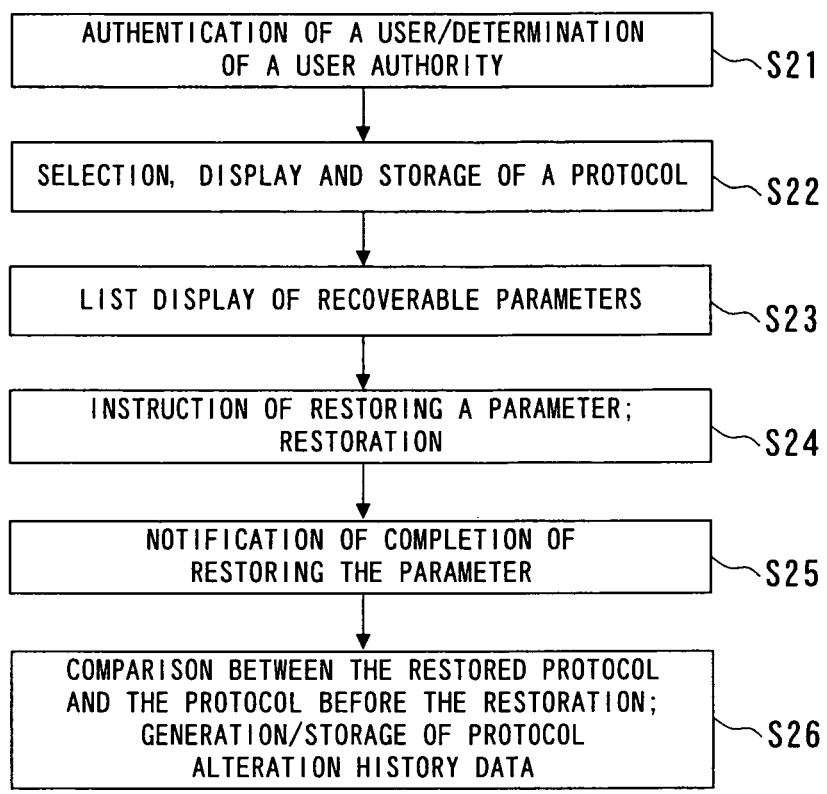
FIG. 9 is a flowchart showing a flow for returning an altered parameter to a parameter before alteration based on protocol alteration history data stored in the protocol alteration history data storage unit by the diagnostic imaging apparatus shown in FIG. 8.

FIG. 9 is a flowchart showing a flow for returning an altered parameter to a parameter before alteration based on protocol alteration history data stored in the protocol alteration history data storage unit 13 by the diagnostic imaging apparatus 1B shown in FIG. 8. The symbols each including S with a number in FIG. 9 indicate steps of the flowchart respectively.

In step S21, a user ID and password of a user are inputted to the user ID input part 5, and the user ID recognizing part 6 determines the user authority. Then, the user authority is notified to the protocol parameter extracting part 8, and the user ID is sent to the restore parameter alteration history extracting part 31.

When the access authority to the protocol is authenticated to the user, the user can display the protocol selecting screen and can select a single or a plurality of arbitrary protocols.

In step S22, the protocol selecting screen is displayed, and the user inputs a request for extracting a protocol, as a restoring target of an altered parameter to the protocol selection part 7 with referring to the displayed protocol selecting screen. Then, the inputted request for extracting the protocol is sent to the protocol parameter extracting part 8. The protocol parameter extracting part 8 refers to the user authority inputted from the user ID recognizing part 6. When the access authority to the requested protocol is authenticated to the user, the protocol parameter extracting part 8 extracts the requested protocol after the alteration, from the protocol data storage unit 4 and sends the extracted protocol to the protocol parameter display part 9 and the protocol parameter storing part 15.

As a consequence thereof, the protocol parameter display part 9 in the user interface 3 displays the selected protocol including the parameter after the alteration. Further, the protocol including the parameter after the alteration is temporarily stored in the protocol parameter storing part 15.

In step S23, the list of the restorable parameters can be displayed on the restore parameter selection part 32. Therefore, the user first can input, to the parameter-before-alteration display requesting part 30, the request for displaying the list of the parameters which can be restored to the parameters before the alteration of the altered parameters. Then, the parameter-before-alteration display requesting part 30 sends the inputted request for displaying the list of the restorable parameters to the restore parameter alteration history extracting part 31.

The restore parameter alteration history extracting part 31 acquires, from the user ID recognizing part 6, information indicating whether or not the access authority corresponding to the user ID to the protocols or parameters is authenticated to the user and extracts, from the protocol alteration history data storage unit 13, the protocol alteration history data including the parameters which can be displayed, be selected, and be restored within the existing range of the access authority in accordance with the request for displaying the list of the parameters. Then, the restore parameter alteration history extracting part 31 sends the list of the restorable parameters based on the extracted protocol alteration history data or the protocol alteration history data to the restore parameter selection part 32. Thus, the restore parameter selection part 32 displays the restorable parameters as a list thereof.

Figure 10:
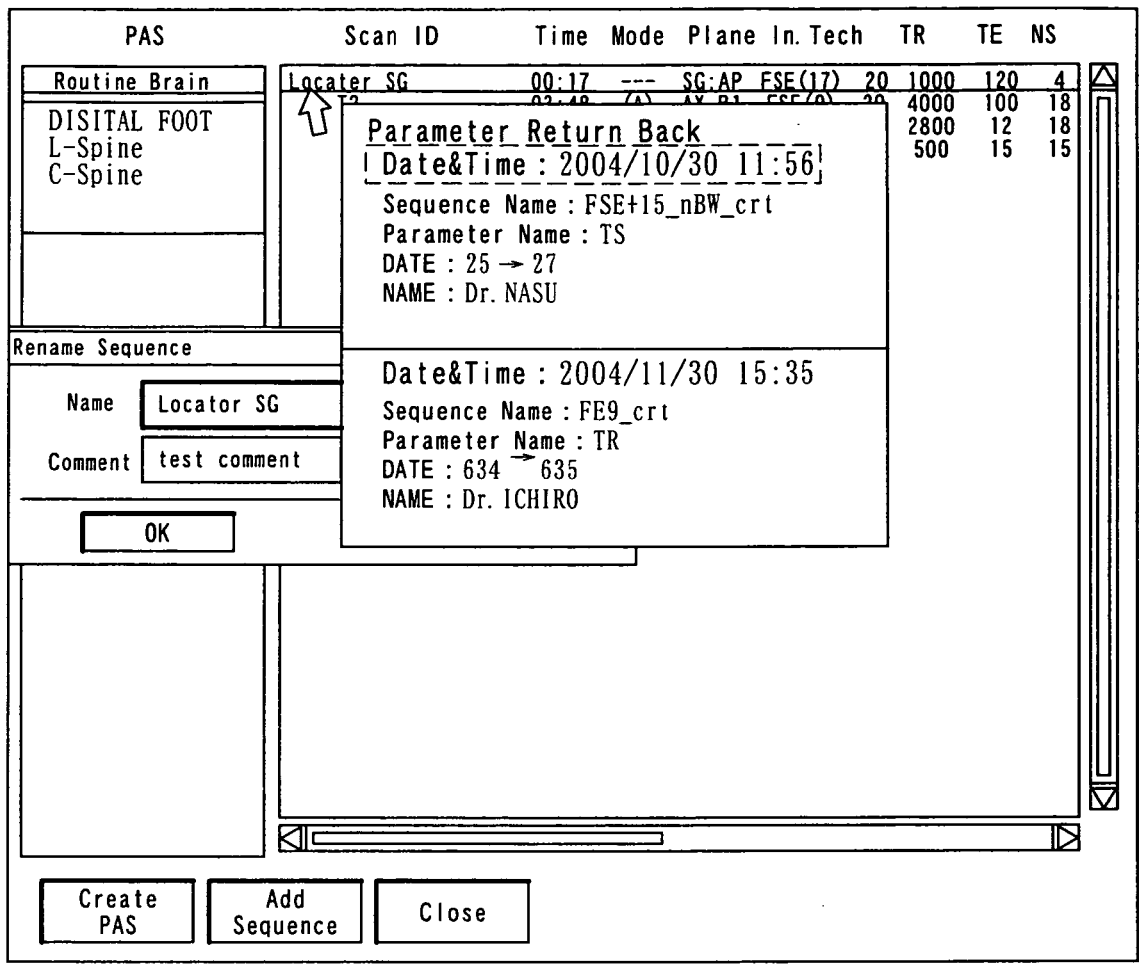
FIG. 10 is a diagram showing an example of recoverable parameters of a protocol displayed on the restore parameter selection part of the diagnostic imaging apparatus shown in FIG. 8.

FIG. 10 is a diagram showing an example of recoverable parameters of a protocol displayed on the restore parameter selection part 32 of the diagnostic imaging apparatus 1B shown in FIG. 8.

Referring to FIG. 10, the cursor selects a specific protocol, thereby displaying the altering date-and-time, the sequence name, the parameter name, the data value after/before the alteration, and the identification information of the user who altered the parameter. This enables the confirming operation of the restorable parameter.

In step S24, the user can send the selecting information (instruction) of the parameter, as a restoring target, to the protocol parameter record part 11 via the restore parameter selection part 32. The parameter can be selected based on the unit of parameter or protocol. Further, the selecting information of the parameter includes the data value of the parameter before the alteration.

Therefore, the protocol parameter record part 11 restores the protocol defined with the parameter before the alteration and updates the protocol stored in the protocol data storage unit 4 to the protocol before the alteration of the parameter.

In step S25, the protocol parameter record part 11 completes the restoration of the protocol stored in the protocol data storage unit 4 and then sends a notification indicating the completion of restoration of the protocol to the protocol parameter alteration history record part 14.

In step S26, the protocol parameter alteration history record part 14 acquires the protocol before the restoration, which is temporarily stored in the protocol parameter storing part 15, and the protocol after the restoration, which is stored in the protocol data storage unit 4, and compares the protocol before the restoration with the protocol after the restoration. Then, as a result of the comparison, the protocol parameter alteration history record part 14 generates the protocol alteration history data about the altered (restored) parameter, and writes the generated protocol alteration history data to the protocol alteration history data storage unit 13. Thus, the protocol alteration history data storage unit 13 stores the new protocol alteration history data indicating a restoration history of the parameter.

Note that information, e.g., the user ID and restoring date-and-time, is properly added to the protocol alteration history data indicating restoration history of a parameter, similarly to the foregoing.

Therefore, the diagnostic imaging apparatus 1B as described above makes it possible to restore the once altered parameters to the original parameters again by using the protocol alteration history data stored in the diagnostic imaging apparatus 1 shown in FIG. 1.

Figure 11:
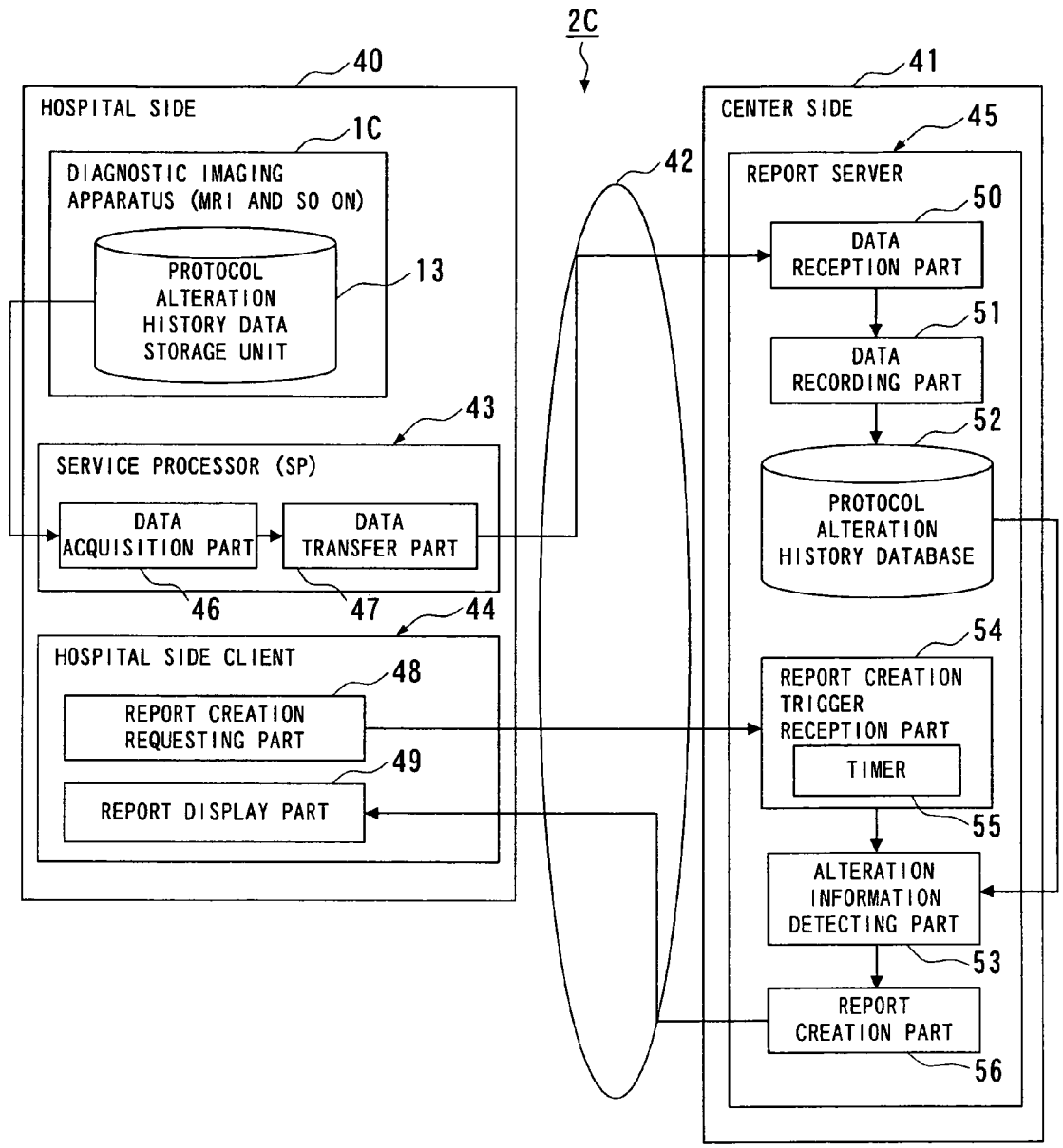
FIG. 11 is a functional block diagram showing a protocol alteration history managing system serving as an example of a medical system according to an embodiment of the present invention.

FIG. 11 is a functional block diagram showing a protocol alteration history managing system serving as an example of a medical system according to an embodiment of the present invention.

A protocol alteration history managing system 2C shown in FIG. 11 is a system for reporting alteration parts of protocols in the gross by generating reports according to protocol alteration information based on protocol alteration history data. The protocol alteration history managing system 2C is an ASP system which connects hospital sides 40 with a center side 41 through networks 42. The method for storing the protocol alteration history data in the protocol alteration history managing system 2C is not different from that of the protocol alteration history managing system 2 mounted in the diagnostic imaging apparatus 1 shown in FIG. 1 substantially. Therefore, the common structure members participating in storage of the protocol alteration history data are not shown and explanations thereof are omitted.

The protocol alteration history managing system 2C includes service processors (SP) 43, hospital side clients 44 and a report server 45. The service processors 43 and the hospital side clients 44 are provided in the hospital sides 40 respectively while the report server 45 is provided in the center side 41. The service processors 43 and the hospital side clients 44 are connected with the report server 45 through the networks 42 respectively. In addition, a single of or a plurality of diagnostic imaging apparatuses 1C is provided in each of the hospital sides 40. Each of the diagnostic imaging apparatuses 1C has the protocol alteration history data storage unit 13 for storing protocol alteration history data individually or in common.

The service processor 43 in the hospital side 40 includes a data acquisition part 46 and a data transfer part 47. The hospital side client 44 includes a report creation requesting part 48 and a report display part 49. The report server 45 in the center side 41 includes a data reception part 50, a data recording part 51, a protocol alteration history database 52, an alteration information detecting part 53, a report creation trigger reception part 54, a timer 55 and a report creation part 56.

Note that, the service processors 43 may be provided in a single or a plurality of diagnostic imaging apparatuses 1C in a plurality of hospitals. In this case, the hospital side clients 44 and the service processors 43 provided in the hospital sides 40 respectively may be connected with the common report server 45.

The data acquisition part 46 on the hospital side 40 has a function for acquiring the protocol alteration history data from the protocol alteration history data storage unit 13, periodically or in accordance with an instruction from an input device (not shown), and a function for sending the acquired protocol alteration history data to the data transfer part 47. The data transfer part 47 has a function for transferring the protocol alteration history data received from the data acquisition part 46 to the data reception part 50 on the center side 41 via the network 42.

The data reception part 50 on the center side 41 has a function for receiving the protocol alteration history data transferred from the data transfer part 47 and a function for sending the received protocol alteration history data to the data recording part 51. The data recording part 51 has a function for writing the protocol alteration history data received from the data reception part 50 to the protocol alteration history database 52. Therefore, the protocol alteration history database 52 stores the protocol alteration history data received by the data reception part 50.

The alteration information detecting part 53 has a function for reading the protocol alteration history data to be used for creation of a report from the protocol alteration history database 52 in accordance with an instruction for creating the report, received as a report creation trigger, from the report creation trigger reception part 54 to detect the protocol alteration information, and sending the created protocol alteration information to the report creation part 56. The detection conditions of the protocol alteration information can be set up dynamically and arbitrarily in a similar way as that on the diagnostic imaging apparatus 1A shown in FIG. 4.

The report creation part 56 has a function for creating the report by using the protocol alteration information received from the alteration information detecting part 53 and a function for transmitting the created report to the report display part 49 on the hospital side 40 via the network 42. Therefore, the report creation part 56 has a calculation function of operation and static data necessary for creating the report and a function for acquiring another data to add to the report, if needed.

The report creation trigger reception part 54 has a function for receiving the report creation trigger for instructing the creation of the report from the report creation requesting part 48 of the hospital side 40 via the network 42, and sending the received report creation trigger to the alteration information detecting part 53. Further, if needed, the timer 55 is arranged, and the report creation trigger reception part 54 thus is configured to send the report creation trigger to the alteration information detecting part 53 without waiting for the reception of the report creation trigger from the report creation requesting part 48, periodically after a lapse of a predetermined time or at a predetermined timing.

The report creation requesting part 48 on the hospital side 40 has a function of the user interface 3, for transmitting the report creation trigger for instructing the creation of the report to the report creation trigger reception part 54 on the center side 41 via the network 42.

The report display part 49 also has a function of the user interface 3, for receiving and displaying the report transmitted from the report creation part 56 on the center side 41 via the network 42.

Next, the operation of the protocol alteration history managing system 2C will be described.

Figure 12:
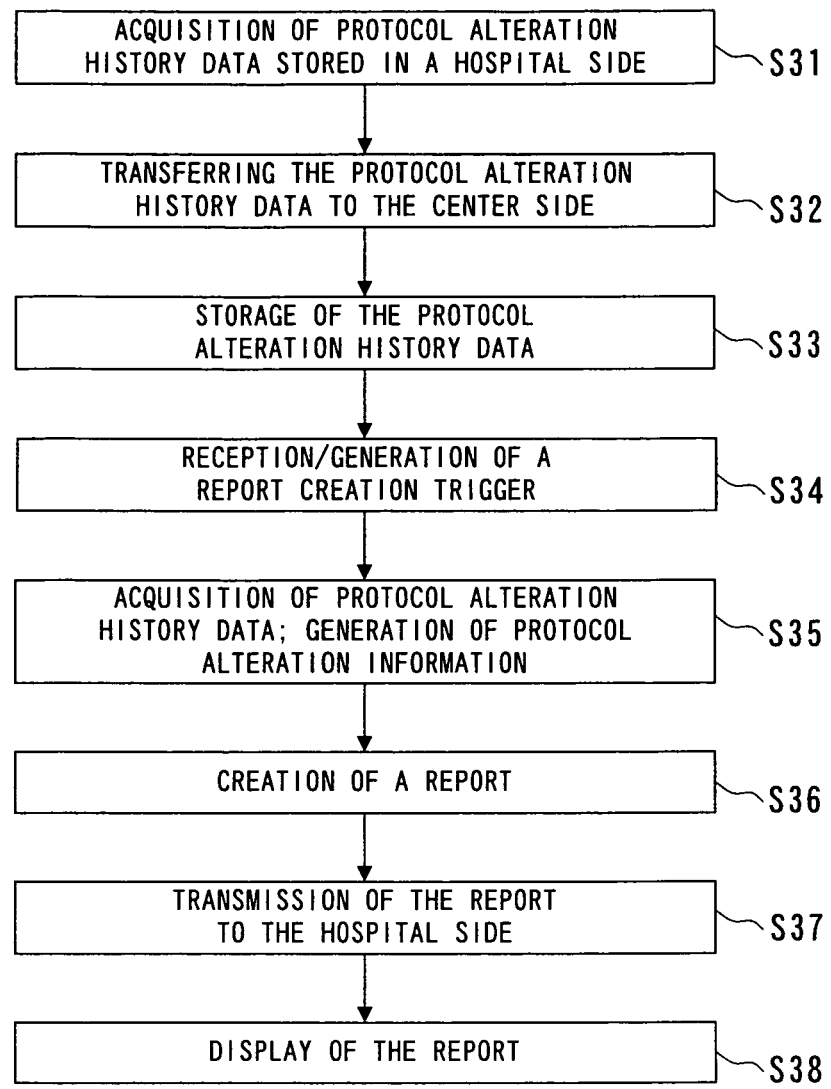
FIG. 12 is a flowchart showing a flow for creating a report using protocol alteration information detected from protocol alteration history data to report an alteration part of a protocol by the protocol alteration history managing system shown in FIG. 11.

FIG. 12 is a flowchart showing a flow for creating a report using protocol alteration information detected from protocol alteration history data to report an alteration part of a protocol by the protocol alteration history managing system 2C shown in FIG. 11. The symbols each including S with a number in FIG. 12 indicate steps of the flowchart respectively.

The protocol alteration history data of the diagnostic imaging apparatus 1C is generated and is stored in the protocol alteration history data storage unit 13 in advance.

In step S31, the data acquisition part 46 on the hospital side 40 acquires necessary protocol alteration history data from a single or a plurality of the protocol alteration history data storage units 13, periodically or in accordance with an instruction from an input device (not shown), and sends the acquired protocol alteration history data to the data transfer part 47.

In step S32, the data transfer part 47 transmits the protocol alteration history data received from the data acquisition part 46 to the data reception part 50 on the center side 41 via the network 42. Then, the protocol alteration history data transferred from the data transfer part 47 is received by the data reception part 50 and is sent to the data recording part 51.

In step S33, the data recording part 51 writes the protocol alteration history data received from the data reception part 50 to the protocol alteration history database 52. Therefore, the protocol alteration history database 52 stores the protocol alteration history data which are periodically transferred from the diagnostic imaging apparatuses 1C on the hospital sides 40.

In step S34, the report creation requesting part 48 on the hospital side 40 transmits the report creation trigger to the report creation trigger reception part 54 via the network 42. Therefore, the report creation trigger transmitted from the report creation requesting part 48 is received by the report creation trigger reception part 54. Alternatively, the report creation trigger reception part 54 generates the report creation trigger periodically or at a predetermined timing by using the timer 55. The report creation trigger reception part 54 sends the report creation trigger to the alteration information detecting part 53.

In step S35, the alteration information detecting part 53 extracts the protocol alteration history data to be used for creation of the report from the protocol alteration history database 52 in accordance with the instruction for creating the report received as the report creation trigger from the report creation trigger reception part 54, and sends the protocol alteration information created using the extracted protocol alteration history data to the report creation part 56.

In step S36, the report creation part 56 creates the report in the form which is designated in advance by using the protocol alteration information received from the alteration information detecting part 53.

FIG. 13 is a diagram showing an example of a report generated by the protocol alteration history managing system 2C shown in FIG. 11.

For example, referring to FIG. 13, a list of weekly altered protocols is displayed in a display form. The report indicates information, such as the name of PAS in which the parameter is altered, the sequence name, the parameter name, the (Old) data value before the alteration, the (New) data value after the alteration, the altering date-and-time, and the identification information of a user who altered the parameter, e.g., the user name and the user ID.

Moreover, in addition to the list of altered protocols, in the case of a week in which the parameter is not altered, information (none) indicating that the protocol in which the parameter is altered does not exist is indicated.

FIG. 14 is a diagram showing another example of a report generated by the protocol alteration history managing system 2C shown in FIG. 11.

For example, referring to FIG. 14, predetermined static data is acquired using the protocol alteration information and examination record data is added, thereby creating an examination history using the protocols (PAS) after alteration, as a report. That is, a top column shown in FIG. 14 indicates a list of the number of use times without altering the parameter and the number of use times with altering the parameter for the protocols shown by the PAS names.

Further, a bottom column shown in FIG. 14 indicates a list of date-and-times (Date, Start time) of examinations using the protocols (PAS) each having the altered parameter, identification information (Study ID) of the examinations, examination regions (Body Region), the PAS names (PAS Name), examination times (Exam Time) and identification information (Scan#) of the scan operations.

As mentioned above, the report creation part 56 can add desired information and can calculate data so as to create a desired report.

In step S37, the report creation part 56 transmits the created report to the report display part 49 on the hospital side 40 via the network 42.

In step S38, the report display part 49 receives and displays the report transmitted from the report creation part 56 on the center side 41 via the network 42. As a result thereof, the user can confirm the report with the hospital side client 44, and can acquire the protocol altering history and desired total information based on the protocol altering history.

Therefore, the protocol alteration history managing system 2C as described above makes it possible to detect protocol alteration information using protocol alteration history data stored in the diagnostic imaging apparatus 1 shown in FIG. 1 to create and display reports indicating desired forms of protocol alteration information. Consequently, a user can refer to the created report to manage alteration history of protocols easily.

Note that, the diagnostic imaging apparatuses 1, 1A, 1B and 1C, and the protocol alteration history managing systems 2, 2A, 2B and 2C according to embodiments as described above may be combined. On the contrary, partially functions of the diagnostic imaging apparatuses 1, 1A, 1B or 1C, or the protocol alteration history managing systems 2, 2A, 2B or 2C may be omitted. For example, users authenticate and acquisition of user's ID may be omitted. In this case, protocol alteration history data may include no identification information of users who altered parameters.

In addition, an element of the diagnostic imaging apparatuses 1, 1A, 1B and 1C may be used as an element of the protocol alteration history managing systems 2, 2A, 2B and 2C. On the contrary, an element of the protocol alteration history managing systems 2, 2A, 2B and 2C may be used as an element of the diagnostic imaging apparatuses 1, 1A, 1B and 1C.

What is claimed is:

1. A medical image diagnostic apparatus, comprising:
   a parameter alteration unit configured to alter a parameter correlated to a desired parameter term from a pre-parameter before altering to a post-parameter after altering, among a plurality of parameters, correlated to respective parameter terms, included in an imaging sequence in accordance with an operation of a user;
   a record control unit configured to record the pre-parameter and the post-parameter, and its parameter term and imaging sequence, into an imaging sequence alteration history storage that is able to store an imaging sequence alteration history including the pre-parameters and the post-parameters, and their parameter terms and imaging sequences;
   an imaging sequence alteration history obtaining unit configured to obtain an imaging sequence alteration history element from out of the imaging sequence alteration history stored in the imaging sequence alteration history storage, the imaging sequence alteration history element indicating alteration in at least one of quality of image, imaging period, and imaging techniques; and
   a display control unit configured to display, based on the obtained imaging sequence alteration history element, an alteration list including the pre-parameters and the post-parameters, and their parameter terms and imaging sequences on a monitor.

2. An apparatus according to claim 1,
   wherein the record control unit is configured to further record its alteration time into the imaging sequence alteration history storage that is able to store the alteration list further including alteration times,
   further comprising a parameter alteration information detecting unit configured to detect parameter alteration information as a part of the imaging sequence alteration history, which is correlated to in a designated period.

3. An apparatus according to claim 1,
wherein the record control unit is configured to further record a user identifier of the user into the imaging sequence alteration history storage that is able to store the alteration list further including user identifiers of respective users,
further comprising a parameter alteration information detecting unit configured to detect parameter alteration information as a part of the imaging sequence alteration history, which is correlated to a desired user identifier.

4. An apparatus according to claim 1,
further comprising a parameter alteration information detecting unit configured to detect parameter alteration information as a part of the imaging sequence alteration history, which is correlated to a desired condition.

5. An apparatus according to claim 1,
wherein the record control unit is configured to further record at least one of its alteration time and user identifier of the user into the imaging sequence alteration history storage that is able to store the alteration list further including at least one of alteration times and user identifiers of respective users, further comprising:
an imaging sequence designation unit configured to designate at least one of a desired time and a desired user identifier in accordance with the operation of the user; and
a parameter alteration information detecting unit configured to detect parameter alteration information as a part of the imaging sequence alteration history, which is correlated to at least one of the designated time and the designated user identifier.

6. An apparatus according to claim 1,
wherein the record control unit is configured to further record its alteration type into the imaging sequence alteration history storage that is able to store the alteration list further including alteration types, further comprising:
an imaging sequence designation unit configured to designate a desired alteration type; and
a parameter alteration information detecting unit configured to detect parameter alteration information as a part of the imaging sequence alteration history, which is correlated to the designated alteration type.

7. A medical image diagnostic apparatus which includes one of an ultrasonic diagnostic apparatus, comprising:
an imaging sequence designation unit configured to designate a desired imaging sequence in accordance with an operation of a user, among a plurality of imaging sequences stored in an imaging sequence storage, an imaging sequence of the imaging sequences includes a plurality of parameters correlated to respective parameter terms;
an imaging sequence extracting unit configured to extract the designated imaging sequence from the imaging sequence storage;
a parameter alteration unit configured to alter a parameter correlated to a desired parameter term of the extracted imaging sequence from a pre-parameter before altering to a post-parameter after altering in accordance with an operation of the user;
a parameter updating unit configured to update the pre-parameter, stored in the imaging sequence storage, corresponding to the extracted imaging sequence to the post-parameter;
a record control unit configured to record the pre-parameter and the post-parameter, and its parameter term and imaging sequence, into an imaging sequence alteration history storage that is able to store an imaging sequence alteration history including the pre-parameters and the post-parameters, their parameter terms and imaging sequences;
an imaging sequence alteration history obtaining unit configured to obtain an imaging sequence alteration history element from out of the imaging sequence alteration history stored in the imaging sequence alteration history storage, the imaging sequence alteration history element indicating alteration in at least one of quality of image, imaging period, and imaging techniques; and
a display control unit configured to display, based on the obtained imaging sequence alteration history element, an alteration list including the pre-parameters and the post-parameters, and their parameter terms and imaging sequences on a monitor.

8. An apparatus according to claim 7,
wherein the record control unit is configured to further record at least one of a name and an identifier of its imaging sequence, a name and an identifier of its parameter term, and a name and an identifier of the user into the imaging sequence alteration history storage that is able to store the alteration list further including at least one of names and identifiers of respective imaging sequences, names and identifiers of respective parameter terms, names and identifiers of respective users.

9. An apparatus according to claim 7, further comprising:
a parameter alteration information detecting unit configured to detect parameter alteration information as a part of the imaging sequence alteration history, which is connected with a desired condition.

10. An apparatus according to claim 7, further comprising:
a reconstruction request unit configured to request reconstruction of the pre-parameter correlated to the designated imaging sequence in accordance with an operation of the user;
an imaging sequence alteration history extracting unit configured to extract the pre-parameter correlated to the designated imaging sequence based on the stored imaging sequence alteration history; and
a parameter restoring unit configured to restore the post-parameter, stored in the imaging sequence storage, to the extracted pre-parameter.

11. An apparatus according to claim 7,
wherein the display control unit is configured to have a different format between the post-parameter and the pre-parameter based on the imaging sequence alteration history so as to identifiably display the post-parameter and the pre-parameter.

12. An apparatus according to claim 9, further comprising:
a using history generating unit configured to generate using history by correlating image sequence using times with user identifiers of the users; and
a using history storage unit configured to store the using history,
wherein the image sequence designation unit is configured to designate an imaging sequence using time and a user identifier in accordance with the operation of the user, and
the parameter alteration information detecting unit is configured to detect parameter alteration information as a part of the imaging sequence alteration history, which is correlated to the designated imaging sequence using time and the designated user identifier.

13. A sequence managing method for a medical image diagnostic apparatus, comprising:

altering a parameter correlated to a desired parameter term from a pre-parameter before altering to a post-parameter after altering, among a plurality of parameters, correlated to respective parameter terms, included in an imaging sequence in accordance with an operation of a user;

recording the pre-parameter and the post-parameter, and its parameter term and imaging sequence, into an imaging sequence alteration history storage that is able to store an imaging sequence alteration history including the pre-parameters and the post-parameters, and their parameter terms and imaging sequences; and obtaining an imaging sequence alteration history element from out of the imaging sequence alteration history stored in the imaging sequence alteration history storage, the imaging sequence alteration history element indicating alteration in at least one of quality of image, imaging period, and imaging techniques; and displaying, based on the obtained imaging sequence alteration history element, an alteration list including the pre-parameters and the post-parameters, and their parameter terms and imaging sequences on a monitor.

14. A sequence managing method for a medical image diagnostic apparatus, comprising:

designating a desired imaging sequence in accordance with an operation of a user, among a plurality of imaging sequences stored in an imaging sequence storage, an imaging sequence of the imaging sequences includes a plurality of parameters correlated to respective parameter terms;

extracting the designated imaging sequence from the imaging sequence storage;

altering a parameter correlated to a desired parameter term of the extracted imaging sequence from a pre-parameter before altering to a post-parameter after altering in accordance with an operation of the user;

updating the pre-parameter, stored in the imagine sequence storage, corresponding to the extracted imaging sequence to the post-parameter;

recording the pre-parameter and the post-parameter, and its parameter term and imaging sequence, into an imaging sequence alteration history storage that is able to store an imaging sequence alteration history including the pre-parameters and the post-parameters, and their parameter terms and imaging sequences;

obtaining an imaging sequence alteration history element from out of the imaging sequence alteration history stored in the imaging sequence alteration history storage, the imaging sequence alteration history element indicating alteration in at least one of quality of image, imaging period, and imaging techniques; and displaying, based on the obtained imaging sequence alteration history element, an alteration list including the pre-parameters and the post-parameters, and their parameter terms and imaging sequences on a monitor.

* * * * *